United States Patent [19]
Kinnersley et al.

[11] Patent Number: 6,083,877
[45] Date of Patent: Jul. 4, 2000

[54] METHODS FOR REGULATING PLANT GROWTH

[75] Inventors: Alan M. Kinnersley, East Lansing; Sarah E. Daniels, Lansing, both of Mich.

[73] Assignee: Auxein Corporation, Lansing, Mich.

[21] Appl. No.: 09/265,172

[22] Filed: Mar. 9, 1999

Related U.S. Application Data

[60] Provisional application No. 60/077,586, Mar. 10, 1998.

[51] Int. Cl.$^7$ ..................................................... A01N 37/44
[52] U.S. Cl. ......................... 504/147; 504/320; 504/326
[58] Field of Search ................................... 504/147, 320, 504/326

[56] References Cited

U.S. PATENT DOCUMENTS

| | | | |
|---|---|---|---|
| 3,712,804 | 1/1973 | Muller et al. | 71/113 |
| 3,869,277 | 3/1975 | Berger et al. | 71/113 |
| 3,887,615 | 6/1975 | Keith et al. | 260/534 M |
| 4,115,105 | 9/1978 | Scannell et al. | 71/113 |
| 4,164,403 | 8/1979 | Ehrenfreund | 71/76 |
| 5,439,873 | 8/1995 | Kinnersley et al. | 504/158 |
| 5,830,919 | 11/1998 | Cohen | 514/561 |

OTHER PUBLICATIONS

Cohen, Yigal et al., "β–Aminobutyric Acid Induces the Accumulation of Pathogenesis–Related Proteins in Tomato (*Lycopersicon esculentum* L.) Plants and Resistance to Late Blight Infection Caused by *Phytophthora infestans*." *Plant Physiol*, vol. 104, pp–59–66 (1994).

*Primary Examiner*—S. Mark Clardy
*Attorney, Agent, or Firm*—Woodard, Emhardt, Naughton Moriarty & McNett

[57] ABSTRACT

Methods for retarding plant growth are described. The methods include treating a plant with 2-aminobutyric acid or a salt thereof, 3-aminobutyric acid or a salt thereof, or a mixture thereof. The compounds may be combined with an additional active agent. The additional active agent may include, for example, a fertilizer, pesticide or an herbicide.

21 Claims, No Drawings

METHODS FOR REGULATING PLANT GROWTH

This application claims priority under 35 USC 119 (e) to U.S. Provisional Application Ser. No. 60/077,586, filed Mar. 10, 1998.

BACKGROUND OF THE INVENTION

The present invention relates generally to the field of plant growth regulators and methods of their use. More specifically, the invention relates to methods of retarding plant growth that include treating a plant with compositions including either 2-aminobutyric acid, 3-aminobutyric acid or a mixture thereof.

In many cases, it is desirable to retard plant growth. For example, maintaining grass found on lawns, sport fields, playgrounds, parks, golf courses, roadsides and cemeteries is costly. Retarding the growth of the grass can reduce maintenance costs by, for example, allowing for a reduction in mowing. Moreover, retarding plant growth is desired for aesthetic reasons. For example, dwarf ornamental plants are aesthetically pleasing and represent a class of plants having significant commercial importance. Furthermore, it may be necessary to control the growth of plants for safety reasons. For example, it may be necessary to retard the growth of plants which are near power lines and railroad rights-of-way.

Several plant growth regulators, such as plant growth retardants, are commercially available. For example, N-phosphonocarbonyl carbamic acid derivatives, carboxyphosphonates, substituted 2,3-dihydro-1,4-oxathin-2,6-dimethylphenoxy, epoxycyclohexane, derivatives of acrylic acid and imidazoline compounds are known. However, use of many of these compounds is cost prohibitive. Moreover, many of these compounds are toxic. There is therefore a need for low-cost, non-toxic plant growth retardants and methods for retarding plants utilizing such retardants. The present invention addresses this need.

SUMMARY OF THE INVENTION

It has been discovered that application of 2-aminobutyric acid or 3-aminobutyric acid to plants results in retardation of plant growth. Accordingly, the invention provides methods for retarding plant growth utilizing these agents.

In one aspect of the invention, a method of retarding plant growth includes treating the plant with a composition including 2-aminobutyric acid or a salt thereof, 3-aminobutyric acid or a salt thereof, or a mixture thereof. The composition may further include one or more additional active agents such as fertilizers, pesticides and herbicides.

Other features of the invention include compositions for retarding plant growth. In one embodiment, the composition includes 2-aminobutyric acid or a salt thereof and at least one additional active agent, such as a fertilizer, pesticide or an herbicide.

In yet another embodiment of the invention, a composition for retarding plant growth is provided that includes 3-aminobutyric acid or a salt thereof and at least one additional active agent, such as a fertilizer, pesticide or an herbicide.

It is an object of the invention to provide methods of retarding plant growth.

It is a further object of the invention to provide compositions for retarding plant growth.

These and other objects and advantages of the present invention will be apparent from the descriptions herein.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As disclosed above, the present invention provides methods for retarding plant growth. It has been discovered that application of 2-aminobutyric acid, 3-aminobutyric acid, or salts thereof to plants results in retardation of plant growth. The invention thus provides methods for retarding plant growth involving the use of either or both of these compounds, and plant growth retardant compositions incorporating effective amounts of these compounds, optionally with one or more additional agricultural agents.

Methods of the invention include treating a plant with 2-aminobutyric acid or a salt thereof, 3-aminobutyric acid or a salt thereof, or a mixture thereof. The composition may further include at least one additional active agent. In the preferred methods of the invention, the plants are typically treated with amounts of the compounds or compositions effective in retarding plant growth. Although the inventive methods may be applied to a wide variety of plants, they are most preferably applied to decorative or ornamental plants as well as trees and turf.

In a first aspect of the invention, a method of retarding plant growth is provided. In one embodiment of the invention, a method of retarding plant growth includes treating the plant with 2-aminobutyric acid or a salt thereof, 3-aminobutyric acid or a salt thereof, or a mixture thereof. The plant is typically treated with an amount of the composition effective in retarding plant growth as described above. The composition may be applied either alone or with a carrier medium as described below.

2-aminobutyric acid and 3-aminobutyric acid may be obtained from commercial sources or may be synthesized by methods known in the art. 2-aminobutyric acid may also be isolated from natural sources by methods known in the art. Any form of these compounds may be used, including active isomers thereof and various salts thereof known to the art. Illustrative carboxylate salts include salts formed from alkali metals, such as sodium and potassium, although others will also be useful.

The amount of 2-aminobutyric acid or 3-aminobutyric acid effective in retarding plant growth will depend on various factors, including the type of plant, the quantity of plants treated and the amount of growth retardation desired. These amounts can be determined by one skilled in the art. However, typical amounts of the compounds used include about 1 ppm to about 24,000 ppm (application rate of about 0.93 g/hectare (g/ha) to about 22 kg/ha), about 1 ppm to about 12,000 ppm (application rate of about 0.93 g/ha to about 11 kg/ha), about 1 ppm to about 10,000 ppm (application rate of about 0.93 g/ha to about 9.3 kg/ha) about 1 ppm to about 7,500 ppm (application rate of about 0.93 g/ha to about 7.1 kg/ha) and about 1 ppm to about 5,000 ppm (application rate of about 0.93 g/ha to about 4.8 kg/ha). The application rates in parentheses above are derived from a treatment utilizing a standard volume of 100 gallons of the specified solutions dispersed over 1 acre. Concentrations of 2-aminobutyric acid or a salt thereof, or 3-aminobutyric or a salt thereof, of from about 1 ppm to about 2,500 ppm (application rate of about 0.93 g/ha to about 2.4 kg/ha) are typically employed, with about 3,000 ppm to about 10,000 ppm (application rate of about 2.8 kg/ha to about 9.3 kg/ha) being most frequently employed.

In a further embodiment, a method of retarding plant growth includes treating the plant with a composition including 2-aminobutyric acid or a salt thereof, 3-aminobutyric acid or a salt thereof, or a mixture thereof, wherein the composition further includes an additional active agent as described below. The compositions may be applied alone but are preferably applied in a carrier medium as described below. The plant is typically treated with an amount of the composition effective in retarding plant growth.

"Active agent" is defined herein to mean an agent that has a beneficial effect on the plant with respect to nutrition, resistance against disease and reduction of plant stress. The active agent may include fertilizers, pesticides, herbicides and other agents affecting plant growth and productivity. The fertilizer may include a wide variety of fertilizers known in the art. Suitable fertilizers are disclosed, for example, in Kirk-Othmer, *Concise Encyclopedia of Chemical Technology*, 4th Ed. v. 10, pp. 433–514(1993). Other greening agents fall within the definition of "active agent" as well, including minerals such as magnesium and iron. The pesticides protect the plant from pests or disease and may be either chemical or biological and include fungicides, bacteriocides, insecticides and anti-viral agents as known in the art.

The amount of the additional active agent included in the composition may vary depending on the nature of the active agent and such amounts are well known to those skilled in the art. One may also follow the directions from the manufacturer of the active agent in determining the amount of additional active agent to use.

The compounds and compositions described above may be preferably combined with a carrier medium as known in the art. The compounds and compositions may, for example, be combined with water, such as tap water or with distilled water to which has been added selected minerals. Alternatively, the compositions of the present invention may be applied as a solid. In such a form, the solid is preferably applied to the soil.

The compositions may further include agricultural additives or formulation aids known to those skilled in the art. Such additives or aids may be used to ensure that the compositions disperse well in a spray tank, stick to or penetrate plant surfaces (particularly leaf or other foliage surfaces) as well as provide other benefits to the plant. For example, surfactants, dispersants, humectants, and binders may be used to disperse the plant retarding compound in a spray tank as well as to allow the compound or compositions to adhere to and/or penetrate the plant surfaces.

The compounds and compositions of the present invention are typically applied to the foliage of the plant but may also be administered as a soil drench. Furthermore, when plants are grown hydroponically, the compounds and compositions may be applied to the aqueous solution in which the plants are grown. The compositions are further preferably applied by spraying. Moreover, the compounds and compositions may also be applied as a seed treatment to slow germination and growth.

The methods, compounds and compositions of the present invention may be used to treat a wide variety of plants, including monocotyledons and dicotyledons, but are most useful with recreational or ornamental plants. For example, the compositions of the present invention may be applied to turf (including rye grass, Bermuda grass, blue grass, fescue) for use in turf management, as well as urban trees. Moreover, the compositions may be used on ornamental plants including poinsettias, chrysanthemums and geraniums where it may be desirable to control the height of the plant and/or produce dwarf plants. Vegetative growth and/or reproductive growth may also be affected.

Reference will now be made to specific examples illustrating the compounds, compositions and methods above. It is to be understood that the examples are provided to illustrate preferred embodiments and that no limitation to the scope of the invention is intended thereby.

EXAMPLE 1

Effect of 2-Aminobutyric acid (2-AB), 3-aminobutyric acid (3-AB) and 4-aminobutyric acid (4-AB) on Growth of Duckweed Duckweed (*Lemna minor L.*) was grown in cultures following the general procedure described in U.S. Pat. 5,439,873. Culture media contained fertilizer alone (basal media) or fertilizer plus glucose (5 g/L) and casein hydrolysate (1 g/L) (growth media). The effects of (DL)-2-AB and (DL)-3-AB were evaluated in both media and compared with the effects of 4-AB (GABA).

TABLE 1

Effect of 2-AB, 3-AB and 4-AB on Growth of Duckweed

|  | Basal Medium | | Growth Medium | |
| --- | --- | --- | --- | --- |
| Treatment | Avg. Dry Wt. (mg) ± SD[†] | % of Control | Avg. Dry Wt. (mg) ± SD[†] | % of Control |
| Control | 10 ± 3 | 100 | 85 ± 4 | 100 |
| 2-AB 1 mM | 5 ± 1 | 50 | 78 ± 1 | 92 |
| 2-AB 5 mM | 2 ± 2 | 80 | 7 ± 1 | 8 |
| 2-AB 10 mM | 2 ± 1 | 80 | 4 ± 1 | 5 |
| 3-AB 1 mM | 3 ± 1 | 70 | 76 ± 2 | 89 |
| 3-AB 5 mM | 2 ± 0 | 80 | 3 ± 2 | 4 |
| 3-AB 10 mM | 1 | 90 | 3 ± 2 | 4 |
| 4-AB 1 mM | 8 ± 1 | 20 | 100 ± 4 | 118 |
| 4-AB 5 mM | 13 ± 1 | 130 | 132 ± 12 | 155 |
| 4-AB 10 mM | 21 ± 5 | 210 | 178 ± 11 | 209 |

[†]Standard Deviation

The results in Table 1 show that, in contrast to 4-AB, which promoted duckweed growth, 2-AB and 3-AB inhibited growth. The results also show that, in both basal and growth media, the effect of 2-AB and 3-AB is the opposite of 4-AB and very inhibitory to plant growth.

EXAMPLE 2

Effect of 2-AB on Growth of Winter Wheat

Winter wheat seeds were germinated and grown as described in U.S. Pat. No. 5,439,873. After 7 days growth, seedlings were sprayed with different amounts of (DL)-2-AB in water. Five days later plants were harvested and dry weights determined. The results are shown in Table 2.

TABLE 2

Effect of 2-AB on Growth of Winter Wheat

| Treatment | Avg. Plant Dry Wt. (g ± SD[†]) | % of Control |
|---|---|---|
| Control | 3.005 ± 0.037 | 100 |
| 2-AB 1,000 ppm | 2.667 ± 0.1 | 89 |
| 2-AB 10,000 ppm | 2.757 ± 0.09 | 92 |

[†]Standard Deviation

Statistical analysis of the data above (with Students t-Test) showed that foliar treatments with 2-AB significantly reduced wheat growth.

EXAMPLE 3

Effect of 2-AB on Growth of Perennial Rye Grass

Perennial rye grass (2.5 g seeds/gallon pot) was germinated and, after two weeks growth, grass was cut and treated with solutions of (DL)-2-AB. One week later, the grass was harvested and dry weights were determined. The results are shown in Table 3.

TABLE 3

Effect of 2-AB on Growth of Perennial Rye Grass

| Treatment | Avg. Grass Dry Wt. (g ± SD[†]) | % of Control |
|---|---|---|
| Untreated Control | 5.6 ± 0.7 | 100 |
| 2-AB 1,000 ppm | 4.6 ± 1.1 | 82 |
| 2-AB 10,000 ppm | 3.6 ± 0.5 | 64 |

[†]Standard Deviation

Results show that, as rye grass was treated with increasing amounts of 2-AB, grass dry weights were progressively inhibited.

EXAMPLE 4

Effect of 2-AB and 3-AB on Growth of Cabbage

Cabbage seedlings were given one drench application 4 days after transplanting when seedlings were 13 days old and were harvested 11 days after treatment application. There were six plants per insert and 2 inserts per repetition, making a total of 12 plants per repetition. Three repetitions were performed per treatment.

TABLE 4

Effect of 2-AB and 3-AB on Growth of Cabbage

| Treatment | Avg. fresh wt. (g ± SD[†]) per 6 plants (insert) | % of Control |
|---|---|---|
| Non-Treated Control | 22.3 ± 1.6 | 100% |
| 2-AB 10,000 ppm 200 ml/insert | 5.1 ± 2.0 | 23% |
| 2-AB 10,000 ppm 100 ml/insert | 12.7 ± 0.2 | 57% |
| 2-AB 5,000 ppm 200 ml/insert | 11.9 ± 2.2 | 53% |
| 2-AB 5,000 ppm 100 ml/insert | 13.9 ± 2.4 | 62% |
| 3-AB 5,000 ppm 100 ml/insert | 4.8 ± 3.1 | 21% |

[†]Standard Deviation

The results in Table 4 show that the treatment with 10,000 ppm 2-AB at 100 ml/insert, and 5,000 ppm 3-AB at 100 ml/insert, significantly inhibited growth in comparison to the other treatments at 95%. 3-AB is more inhibitory (active) than 2-AB as it gave similar results at half the concentration and half the rate. All treatments were significantly inhibited at the 99% confidence level. These results support the proposition that 2-AB and 3-AB can be inhibitory when applied as a drench application.

EXAMPLE 5

Effect of 2-AB and 3-AB on Growth of Kentucky Blue Grass

Kentucky blue grass seed was sown in 5.5" pots and cut twice using electric shear to 1" above soil level. Using a single drench application with selected rates and volumes, grass clippings were collected two weeks after application. Grass clippings were collected in the way that grass was initially cut and fresh weights were recorded. The results are shown in Table 5.

TABLE 5

Effect of 2-AB and 3-AB on Growth of Kentucky Blue Grass

| Treatment | Fresh weight (g) | % of Control | % Reduction |
|---|---|---|---|
| Control | 8.2 | 100% | 0% |
| 2-AB 10,000 ppm 200 ml | 2.0 | 24% | 76% |
| 2-AB 10,000 ppm 100 ml | 3.9 | 48% | 52% |
| 2-AB 5,000 ppm 200 ml | 2.7 | 33% | 67% |
| 2-AB 5,000 ppm 100 ml | 6.2 | 76% | 24% |
| 2-AB 3,000 ppm 200 ml | 5.1 | 62% | 38% |
| 2-AB 3,000 ppm 100 ml | 8.2 | 100% | 0% |
| 3-AB 5,000 ppm 100 ml | 5.2 | 64% | 36% |

The results in Table 5 show that 2-AB is very effective at inhibiting growth of Kentucky Blue Grass at high rates. The higher the concentration of 2-AB applied, the more growth was inhibited. Higher volumes also appear to be an important contribution to the growth inhibition.

The data in Table 5 also show that 3-AB is more effective at inhibiting growth than 2-AB at similar rates and volumes. Similar results were seen in the Duckweed experiments. The growth inhibition effects continued to be visible for several weeks after treatment application.

EXAMPLE 6

Effect of Compositions Including 2-AB, 3-AB and an Additional Active Agent on Retardation of Plant Growth Plants can be prepared as described in Examples 1–3 above. The plants can then be treated with 2-AB and a fertilizer, such as a complete fertilizer containing both micronutrients and micronutrients, such as Peter's Professional All-Purpose Plant Food, water soluble 20/20/20 NPK. The composition can include about 1 ppm to about 10,000 ppm of 2-AB (application rate of about 0.93 g/ha to about 9.3 kg/ha) and about 1 tablespoon of the fertilizer per gallon water. The composition may further include 3-AB at concentrations of about 1 ppm to about 10,000 ppm.

Alternatively, the composition can include 2-AB and 3-AB in water at the aforementioned concentrations.

Other compositions may include as an additional active agent a pesticide or herbicide. The pesticide and herbicide can be included either alone, together with a fertilizer or a mixture thereof. The pesticide can be included in the composition at concentrations denoted by the manufacturer of the pesticide and as known in the art. The compositions described in this Example are useful for retarding plant growth.

While the invention has been illustrated and described in detail in the Examples and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method of retarding plant growth, comprising treating the plant with 2-aminobutyric acid or a salt thereof, 3-aminobutyric acid or a salt thereof, or a mixture thereof, in an amount effective to retard growth of the plant.

2. The method of claim 1, wherein said treating is with a composition that includes about 1 ppm to about 24,000 ppm 2-aminobutyric acid in a carrier medium.

3. The method of claim 2, wherein said composition includes about 1 ppm to about 10,000 ppm 2-aminobutyric acid.

4. The method of claim 1, wherein said treating is with a composition that includes about 1 ppm to about 24,000 ppm 3-aminobutyric acid in a carrier medium.

5. The method of claim 4, wherein said composition includes about 1 ppm to about 10,000 ppm 3-aminobutyric acid.

6. The method of claim 1, wherein said treating is with 2-aminobutyric acid or a salt thereof, 3-aminobutyric acid or a salt thereof, or a mixture thereof, in a carrier medium.

7. The method of claim 6, wherein said carrier medium is water.

8. The method of claim 1, wherein said treating is with a composition that includes at least one additional active agent.

9. The method of claim 8, wherein said active agent is selected from the group (consisting of fertilizers, pesticides and herbicides.

10. The method of claim 9, wherein the active agent is a fertilizer.

11. The method of claim 9, wherein the active agent is a pesticide.

12. The method of claim 11, wherein the pesticide is an antifungal agent.

13. The method of claim 11, wherein the pesticide is an anti-viral agent.

14. The method of claim 11, wherein the pesticide is a bactericide.

15. The method of claim 11, wherein the pesticide is an insecticide.

16. The method of claim 9, wherein the active agent is an herbicide.

17. The method of claim 1, wherein said treating includes applying 2-aminobutyric acid or a salt thereof, 3-aminobutyric acid or a salt thereof, or a mixture thereof, to foliage of said plant.

18. The method of claim 1, wherein said treating includes applying 2-aminobutyric acid or a salt thereof, 3-aminobutyric acid or a salt thereof, or a mixture thereof, to soil.

19. The method of claim 1, wherein said treating includes spraying 2-aminobutyric acid or a salt thereof, 3-aminobutyric acid or a salt thereof, or a mixture thereof, onto the plant.

20. The method of claim 1, wherein said treating includes spraying 2-aminobutyric acid or a salt thereof, 3-aminobutyric acid or a salt thereof, or a mixture thereof, onto a seed as a seed coating.

21. The method of claim 1, wherein said treating includes applying 2-aminobutyric acid or a salt thereof, 3-aminobutyric acid or a salt thereof, or a mixture thereof, to an aqueous solution in which plants are grown hydroponically.

* * * * *

UNITED STATES PATENT AND TRADEMARK OFFICE
CERTIFICATE OF CORRECTION

PATENT NO : 6,083,877
DATED : July 4, 2000
INVENTOR(S) : Kinnersley et al.

It is certified that error appears in the above-identified patent and that said Letters Patent are hereby corrected as shown below:

In column 8, line 16, please delete "bactericide" and insert in lieu thereof --bacteriocide--.

Signed and Sealed this

First Day of May, 2001

*Attest:*

NICHOLAS P. GODICI

*Attesting Officer*     *Acting Director of the United States Patent and Trademark Office*